United States Patent
Böhm et al.

(10) Patent No.: US 6,890,377 B2
(45) Date of Patent: May 10, 2005

(54) THERMOCHROMIC RYLENE DYES

(75) Inventors: Arno Böhm, Mannheim (DE); Matthias Krieger, Mannheim (DE); Stefan Becker, Mannheim (DE); Klaus Müllen, Koeln (DE)

(73) Assignees: BASF Aktiengesellschaft, Ludwigshafen (DE); Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 61 days.

(21) Appl. No.: 10/468,016
(22) PCT Filed: Feb. 14, 2002
(86) PCT No.: PCT/EP02/01573
§ 371 (c)(1),
(2), (4) Date: Aug. 22, 2003
(87) PCT Pub. No.: WO02/068538
PCT Pub. Date: Sep. 6, 2002

(65) Prior Publication Data
US 2004/0089199 A1 May 13, 2004

(30) Foreign Application Priority Data
Feb. 22, 2001 (DE) .......................... 101 08 601

(51) Int. Cl.[7] .............. C09D 11/00; C09B 5/62
(52) U.S. Cl. ............... 106/31.47; 106/31.32; 106/31.2; 546/26; 546/28; 546/38; 546/100; 524/89; 524/90
(58) Field of Search ........... 106/31.47, 31.32, 106/31.2; 546/26, 28, 38, 100; 524/89, 90

(56) References Cited

U.S. PATENT DOCUMENTS

| | | | | |
|---|---|---|---|---|
| 5,405,962 A | * | 4/1995 | Muellen et al. | 546/27 |
| 5,561,232 A | * | 10/1996 | Hao et al. | 546/38 |
| 5,650,513 A | * | 7/1997 | Langhals et al. | 546/38 |
| 5,808,073 A | * | 9/1998 | Bohm et al. | 546/39 |
| 5,986,099 A | * | 11/1999 | Mullen et al. | 546/26 |
| 6,143,905 A | * | 11/2000 | Bohm et al. | 549/232 |
| 6,486,319 B1 | * | 11/2002 | Bohm et al. | 546/38 |
| 6,491,749 B1 | * | 12/2002 | Langhals et al. | 106/31.47 |
| 2004/0068114 A1 | * | 4/2004 | Krieger et al. | 546/28 |

FOREIGN PATENT DOCUMENTS

| | | |
|---|---|---|
| DE | 195 12 773 | 10/1996 |
| DE | 198 48 555 | 4/2000 |
| DE | 101 08 156 | 8/2002 |
| EP | 0 596 292 | 5/1994 |
| EP | 0 648 817 | 4/1995 |
| EP | 0 657 436 | 6/1995 |
| WO | 96/22331 | 7/1996 |
| WO | 96/22332 | 7/1996 |
| WO | 97/22607 | 6/1997 |
| WO | 00/52099 | 9/2000 |
| WO | 01/16109 | 3/2001 |

OTHER PUBLICATIONS

Yves Geerts et al.: "Quaterrylenebis(dicarboximide)s: near infrared absorbing and emitting dyes" J. Mater. Chem., vol. 8, No. 11, pp. 2357–2369, Oct. 1998.
Dyes and Pigments, vol. 16, pp. 19–25 1991, no month available.
Liebigs Annalen, pp. 1229–1244 1995, no month available.
Yuki Gosei Kagaku Kyokaishi, vol. 12, pp. 504–508 1956 with Chemical Abstract 51:8052a, no month available.

* cited by examiner

Primary Examiner—Helene Klemanski
(74) Attorney, Agent, or Firm—Oblon, Spivak, McClelland, Maier & Neustadt, P.C.

(57) ABSTRACT

Rylene dyes of the general formula I

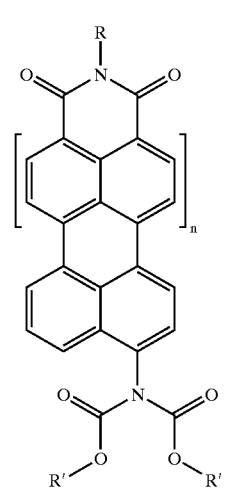

where
R is hydrogen; unsubstituted or substituted $C_1$–$C_{30}$-alkyl, aryl or hetaryl;
R' is unsubstituted or substituted $C_2$–$C_{30}$-alkyl or $C_5$–$C_8$-cycloalkyl, or substituted methyl;
n is 0 or 1,
their preparation and use for coloring high-molecular-weight organic and inorganic materials, and aminorylene-3,4-dicarboximide of the formula IV as their intermediates.

14 Claims, No Drawings

THERMOCHROMIC RYLENE DYES

The present invention relates to novel rylene dyes of the general formula I

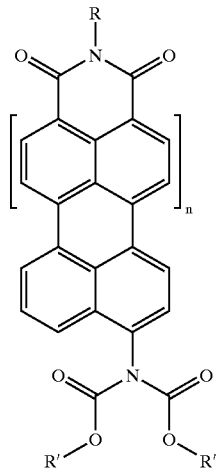

where
R is hydrogen;
$C_1$–$C_{30}$-alkyl, whose carbon chain may be interrupted by one or more —O—, —S—, —$NR^1$—, —CO— and/or —$SO_2$— groups and which may be monosubstituted or polysubstituted by cyano, $C_1$–$C_6$-alkoxy, aryl, which may be substituted by $C_1$–$C_{18}$-alkyl or $C_1$–$C_6$-alkoxy, and/or a 5- to 7-membered heterocyclic radical which is bonded via a nitrogen atom and may contain further heteroatoms and may be aromatic;
aryl or hetaryl, each of which may be monosubstituted or polysubstituted by $C_1$–$C_{18}$-alkyl, $C_1$–$C_6$-alkoxy, cyano, —$CONHR^2$, —$NHCOR^2$ and/or aryl- or hetarylazo, each of which may be substituted by $C_1$–$C_{10}$-alkyl, $C_1$–$C_6$-alkoxy and/or cyano;
R' is $C_2$–$C_{30}$-alkyl, whose carbon chain may be interrupted by one or more —O— and/or —CO— groups and which may be monosubstituted or polysubstituted by cyano, $C_1$–$C_6$-alkoxy, $C_5$–$C_8$-cycloalkyl, whose carbon skeleton may be interrupted by one or more —O—, —S— and/or —$NR^1$— groups and which may be $C_1$–$C_6$-alkyl-substituted, aryl, which may be substituted by $C_1$–$C_{18}$-alkyl or $C_1$–$C_6$-alkoxy, and/or a 5- to 7-membered heterocyclic radical which is bonded via a nitrogen atom and which may contain further heteroatoms and which may be aromatic;
methyl, which is monosubstituted or disubstituted by aryl, hetaryl and/or $C_5$–$C_8$-cycloalkyl, each of which may be substituted by $C_1$–$C_{18}$-alkyl or $C_1$–$C_6$-alkoxy;
$C_5$–$C_8$-cycloalkyl, whose carbon skeleton may be interrupted by one or more —O—, —S— and/or —$NR^1$— groups and which may be monosubstituted or polysubstituted by $C_1$–$C_6$-alkyl;
$R^1$ is hydrogen or $C_1$–$C_6$-alkyl;
$R^2$ is hydrogen; $C_1$–$C_{18}$-alkyl; aryl or hetaryl, each of which may be substituted by $C_1$–$C_6$-alkyl, $C_1$–$C_6$-alkoxy and/or cyano;
n is 2 or 3,
and to the preparation of these dyes, and to their use for coloring high-molecular-weight organic and inorganic materials.

The present invention furthermore relates to novel aminorylene-3,4-dicarboximides of the general formula IV

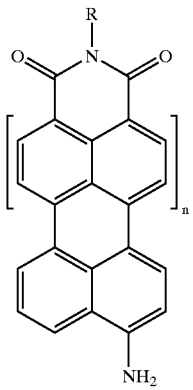

as intermediates for the rylene dyes (I).

Perylene-3,4-dicarboximides which are substituted on the imide nitrogen atom, unsubstituted perylene-3,4-dicarboximide and perylene-3,4-dicarboximides which are substituted on the perylene skeleton are suitable not only as pigment precursors, but are themselves also advantageously employed as pigments and fluorescent dyes. The perylene-3,4-dicarboximides substituted on the perylene skeleton which have been disclosed hitherto are substituted in the 1,6-, 1,7-, 1,6,9-, 1,7,9- and 1,6,7,12-position and also only in the 9-position. The perylene skeleton in each case carries a halogen atom, in particular a bromine atom, in the 9-position (WO-A-96/22331, EP-A-596 292 and WO-A-97/22607 and the references cited therein, and Dyes and Pigments 16, pages 19–25 (1991)). EP-A-657 436 and Liebigs Annalen 1995, pages 1229–1244, also describe an N-(1-hexylheptyl)-9-aminoperylene-3,4-dicarboximide which is prepared by nitrating the corresponding N-substituted perylene-3,4-dicarboximide using dinitrogen tetraoxide followed by reduction with metallic iron in the presence of hydrochloric acid. However, this process is restricted to perylene-3,4-dicarboximides carrying unsubstituted alkyl groups on the imide nitrogen atom and gives exclusively isomer mixtures (1- and 9-isomers), which are difficult to purify, in low yields. Corresponding N-substituted 4-aminonaphthalene-1,8-dicarboximides are disclosed in Yuki Gosei Kagaku Kyokaishi 12, pages 504–508 (1956) (see Chemical Abstracts 51:8052a (1957)).

EP-A-648 817 describes fluorescent dyes containing imide groups whose imide nitrogen atom, for reversible solubilization, has been converted into a carbamate function, which renders the dye soluble in the application medium and can be re-cleaved thermally. Inter alia, unsubstituted perylene-3,4-dicarboximide whose NH function is reacted correspondingly is also listed here as fluorescent dye. Since the solubilization takes place via the imide nitrogen atom there is no possibility of modifying the dye on the nitrogen atom by specific substitution. In addition, the hue of the dye does not change on thermal removal of the alkoxycarbonyl protecting group, and the dye is therefore not thermochromic.

WO-A-01/16169, unpublished at the priority date of the present invention, describes shorter homologs of the rylene dyes of the invention based on naphthalene- and perylene-3,4-dicarboxylic acid derivatives. These homologs, however, cover only the shorter-wave color space.

It is an object of the present invention to provide further dyes having advantageous applicational properties which can in particular not only be incorporated readily into the respective application medium and matched to this medium, but are also thermochromic and absorb in the red and infrared region of the electromagnetic spectrum.

We have found that this object is achieved by the rylene dyes of the formula I defined at the outset.

Preferred rylene dyes are given in the subclaims.

We have also found a process for the preparation of the rylene dyes of the general formula I which comprises a) reacting a bromorylene-3,4-dicarboximide of the general formula II

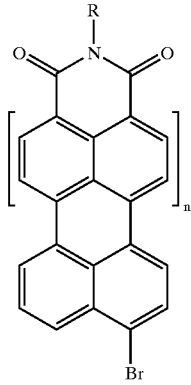

with a benzophenonimine of the general formula III

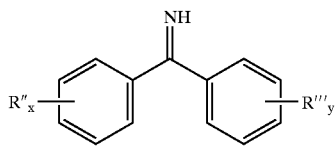

where

R", R''', independently of one another, are hydrogen, $C_1$–$C_6$-alkyl or $C_1$–$C_6$-alkoxy and x, y, independently of one another, are an integer from 1 to 3, in the presence of an aprotic organic solvent, a transition-metal catalyst system and a base in an aryl-N coupling reaction;

b) hydrolyzing the resultant ketimine in the presence of an acid and in the presence of a polar, aprotic solvent to give an aminorylene-3,4-dicarboximide of the general formula IV

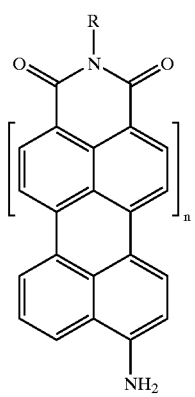

and c) subsequently reacting the latter with a dicarbonate of the general formula V

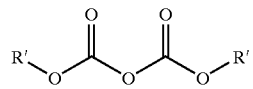

in the presence of a polar, aprotic solvent and in the presence of a base to give the rylene dye I.

We have also found a process for the preparation of aminorylene-3,4-dicarboximides of the general formula IV, which comprises a) reacting a bromorylene-3,4-dicarboximide of the general formula II with a benzophenonimine of the general formula III in the presence of an aprotic organic solvent, a transition-metal catalyst system and a base in an aryl-N coupling reaction to give the corresponding ketimine, and b) subsequently hydrolyzing the latter in the presence of an acid and in the presence of a polar, aprotic solvent.

In addition, we have found the aminorylene-3,4-dicarboximides of the general formula IV as intermediates for the rylene dyes of the general formula I.

Not least, we have found the use of the rylene dyes of the general formula I for coloring high-molecular-weight organic and inorganic materials.

All the alkyl groups which occur in the formulae I to V can be either straight-chain or branched. If the alkyl groups are substituted, they generally carry 1 or 2 substituents. Substituted aromatic radicals can generally have up to 3, preferably 1 or 2, of said substituents. Preferred aryl radicals are naphthyl and in particular phenyl.

Examples which may be mentioned of suitable radicals R, R', R", R''', $R^1$ and $R^2$ (and their substituents) are detailed below:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above names isooctyl, isononyl, isodecyl and isotridecyl are trivial names and originate from the alcohols obtained in the oxosynthesis);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 4,7-dithiaoctyl, 4,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

propan-2-on-1-yl, butan-3-on-1-yl, butan-3-on-2-yl and 2-ethylpentan-3-on-1-yl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

cyanomethyl, 2-cyanoethyl, 3-cyanopropyl, 2-methyl-3-ethyl-3-cyanopropyl, 7-cyano-7-ethylheptyl and 4-methyl-7-methyl-7-cyanoheptyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

formylamino, acetylamino, propionylamino and benzoylamino;

phenylazo, 2-naphthylazo, 2-pyridylazo and 2-pyrimidylazo;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl and 2,4,6-tri-sec-butylphenyl, 2-, 3- and 4-tert-butylphenyl, 2,4-, 2,5-, 3,5- and 2,6-di-tert-butylphenyl, 2,4,6-tri-tert-butylphenyl; 2,3- and 4-methoxyphenyl, 2,4-, 2,5-, 3,5- and 2,6-dimethoxyphenyl, 2,4,6-trimethoxyphenyl, 2,3- and 4-ethoxyphenyl, 2,4-, 2,5-3,5- and 2,6-diethoxyphenyl, 2,4,6-triethoxyphenyl, 2,3- and 4-propoxyphenyl, 2,4-, 2,5-, 3,5- and 2,6-dipropoxyphenyl, 2,3- and 4-isopropoxyphenyl, 2,4-, 2,5-, 3,5- and 2,6-diisopropoxyphenyl and 2,3- and 4-butoxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-N-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl, 3-, 4- and 5-propylcyclooctyl, 2-dioxanyl, 4-morpholinyl, 2- and 3-tetrahydrofuryl, 1-, 2- and 3-pyrrolidinyl and 1-, 2-, 3- and 4-piperidyl.

The rylene dyes of the general formula I can advantageously be prepared by the multistep process according to the invention, in which, in step a) a bromorylene-3,4-dicarboximide of the general formula II is reacted with a benzophenonimine of the general formula III to give a ketimine, in step b), the ketimine is hydrolyzed under acidic conditions to give the aminorylene-3,4-dicarboximide of the general formula IV, and the latter is subsequently reacted, in step c), with a dicarbonate of the formula V to give the rylene dye of the general formula I.

The terrylene- and/or quaterrylene-3,4-dicarboximides II, brominated in the peri position and used as starting materials in step a), are known from prior German patent application 101 08 156.1 and may be prepared by the following, three-stage process described therein:

a') one-sided alkaline saponification of an asymmetric rylenetetracarboxylic diimide of the formula VI

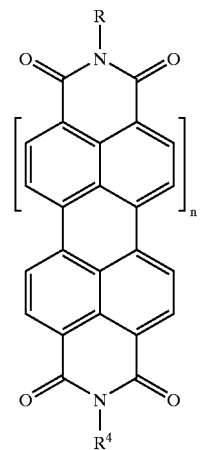

VI in which $R^4$ is $C_5$–$C_8$-cycloalkyl whose carbon framework may be interrupted by one or more groups —O—, —S— and/or —$NR^2$— and which may be substituted one or more times by $C_1$–$C_6$-alkyl, in the presence of a polar organic solvent, b') one-sided decarboxylation of the rylenetetracarboxylic monoimide monoanhydride formed in step a'), of the formula VII

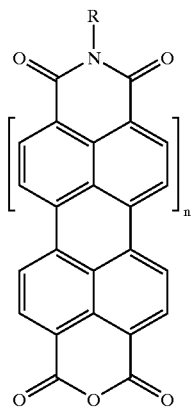

in the presence of a tertiary nitrogen-basic compound and of a transition metal catalyst, and c') reaction of the peri-unsubstituted rylene-3,4-dicarboximide of the formula VIII

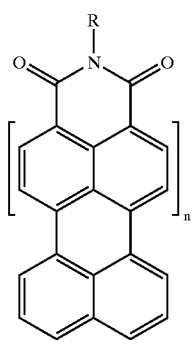

with elemental bromine.

Polar solvents suitable for step a') of this process are, in particular, branched $C_3$–$C_6$ alcohols, such as isopropanol, tert-butanol and 2-methyl-2-butanol.

In general, from 40 to 200 g of solvent are employed per g of VI.

Suitable bases are inorganic bases, especially alkali metal and alkaline earth metal hydroxides, e.g. sodium hydroxide and potassium hydroxide, which are used preferably in the form of aqueous solutions or suspensions (generally with a concentration or strength of from 50 to 80% by weight), and organic bases, especially alkali metal and alkaline earth metal alkoxides, with preference being given to sodium and potassium alkoxides, such as sodium methylate, potassium methylate, potassium isopropylate and potassium tert-butylate, which are commonly used in anhydrous form.

In general from 5 to 50 equivalents of base, based on VI, are required.

The reaction temperature is generally from 50 to 120° C., preferably from 60 to 100° C.

The saponification is normally concluded in from 10 to 40 h.

In step b') of this process, the rylene tetracarboxylic monoimide monohydrides VII are one-sidedly decarboxylated in the presence of a tertiary nitrogen-basic compound as solvent and of a transition metal catalyst.

Particularly suitable solvents are high-boiling nitrogen bases, e.g. cyclic amides, such as N-methylpyrrolidone, and aromatic heterocycles, such as quinoline, isoguinoline and quinaldine.

Customary solvent amounts are from 20 to 150 g per g of VII.

Particularly suitable catalysts are the transition metals copper and zinc and also in particular their organic and inorganic salts, which are preferably used in anhydrous form.

Examples of preferred salts are copper(I) oxide, copper(II) oxide, copper(I) chloride, copper(II) acetate, zinc acetate and zinc propionate, particular preference being given to copper(I) oxide and zinc acetate.

It is of course also possible to use mixtures of said catalysts.

In general from 50 to 90 mol % of catalyst, based on VII, are employed.

The reaction temperature is generally from 100 to 250° C., in particular from 160 to 200° C. It is advisable to operate using an inert gas atmosphere (e.g. nitrogen).

The decarboxylation is normally over in from 3 to 20 h.

Step c') of this process, the regioselective bromination of the rylene-3,4-dicarboximide VIII, is preferably conducted in an aliphatic monocarboxylic acid, particularly a $C_1$–$C_4$-carboxylic acid, such as formic acid, acetic acid, propionic acid, butyric acid or mixtures thereof, or in a halogenated, aliphatic or aromatic solvent, such as methylene chloride, chloroform or chlorobenzene.

It is normal to use from 5 to 30 g, preferably from 15 to 25 g, of solvent per g of VIII that is to be brominated.

In general, the presence of a halogenating catalyst is not necessary. However, if it is desired to accelerate the bromination reaction (for example by a factor of 1.5 to 2), it is advisable to add elemental iodine, preferably in an amount of from 1 to 5 mol %, based on VIII.

The molar ratio between bromine and VIII is generally from about 1:1 to 5:1, preferably from 3:1 to 4:1.

The reaction temperature is generally from 0 to 70° C., preferably from 10 to 40° C.

Depending on the reactivity of the substrate of the general formula VIII and the presence or absence of iodine, the bromination is usually complete in from 2 to 12 hours.

Step a) of the present, inventive process, the reaction of the bromorylene-3,4-dicarboximide II with a benzophenone III in an aryl-N coupling reaction to give a ketimine, is conducted in the presence of an aprotic organic solvent, a transition metal catalyst system and a base.

Suitable benzophenonimines of the general formula III for the ketimine formation are, in particular, benzophenonimine, 4,4'-dimethyl- and 4,4'-diethylbenzophenonimine, 2,2',4,4'-tetramethylbenzophenonimine and 4,4'-dimethoxy- and 4,4'-diethoxybenzophenonimine, benzophenonimine itself being preferred.

In general, from 1 to 4 mol, preferably from 1.5 to 2.5 mol, of III are employed per mole of II.

Particularly suitable aprotic organic solvents are anhydrous, inert, aromatic solvents, such as benzene and its alkylation products, for example toluene and o-, m- and p-xylene, and mixtures of these compounds.

The amount of solvent is usually from 50 to 300 kg, preferably from 100 to 200 kg, per kg of II.

Particularly suitable transition-metal catalysts are palladium compounds, where palladium(0) and palladium(II) complexes, such as tris(dibenzylideneacetone)dipalladium (0), dichloro[1,1'-bis(diphenylphosphino)ferrocene]palladium(II) and dichloro(1,5-cyclooctadiene)palladium(II), and palladium(II) acetate may be mentioned as preferred examples.

The transition-metal catalyst is usually employed in an amount of from 0.5 to 5 mol %, especially from 1 to 3 mol %, based on II.

In addition, a phosphine-based cocatalyst is preferably employed. Preferred examples thereof are bidentate phosphine ligands, such as racemic 2,2'-bis(diphenylphosphino)-1,1'-binaphthyl, 1,1'-bis(diphenylphosphino)ferrocene, 1,1'-bis(di-o-tolylphosphino)ferrocene, 1,1'-bis(di-p-methoxyphenylphosphino)ferrocene and 2,2'-bis(di-o-tolylphosphino)-diphenylether, and phosphines which act as monodentate phosphine ligands, such as tri-o-tolylphosphine, tri-tert-butylphosphine and triphenylphosphine.

Suitable amounts of cocatalyst are generally from 1 to 5 mol %, preferably from 1 to 3 mol %, based on the transition-metal catalyst.

Particularly suitable bases are alkali metal amides, especially alkali metal di($C_3$–$C_6$-alkyl)amides, and alkali metal alkoxides, especially the alkali metal salts of secondary and tertiary aliphatic ($C_3$–$C_6$)-alcohols. Preferred examples of these bases are lithium diisopropylamide, sodium diisopropylamide and potassium diisopropylamide, and lithium isopropoxide, sodium iospropoxide, potassium isopropoxide, lithium tert-butoxide, sodium tert-butoxide and potassium tert-butoxide, particular preference being given to sodium tert-butoxide and potassium tert-butoxide.

In general, an amount of base which his equimolar to the benzophenonimine of the general formula III is employed.

The reaction temperature is usually from 50 to 140° C., preferably from 70 to 120° C.

Depending on the reactivity of the brominated rylene-3,4-dicarboximide of the general formula II and the amount of catalyst employed, the reaction time is generally from 10 to 24 hours.

An advantageous technical procedure in step a) is the following:

The solvent, catalyst and cocatalyst are initially introduced under a protective-gas atmosph re, the bromorylene-3,4-dicarboximide of the general formula II, the benzophenonimine of the general formula III and the base are added successively with stirring, and the mixture is heated at the desired reaction temperature under a protective gas for from to 24 hours. After the mixture has been cooled to room temperature, the solid constituents are filtered off, and the solvent is removed by distillation under reduced pressure.

The purity of the resultant ketimine is generally adequate for further processing. If desired, the crude product can be purified further by re-precipitation from a mixture of chloroform or methylene chloride and petroleum ether or by column chromatography on silica gel using chloroform as eluent.

Step b) of the process according to the invention, the hydrolysis of the ketimine to give aminorylene-3,4-dicarboximide of the general formula IV, is carried out in the presence of a polar, aprotic solvent. Preferred solvents are aliphatic ethers, where acrylic ethers, such as, in particular, di($C_2$–$C_4$-alkyl)ethers and $C_2$–$C_3$-alkyleneglycol di-$C_1$–$C_2$-alkylethers, and cyclic ethers are suitable. The following particularly preferred ethers may be mentioned by way of example: diethylether, dipropylether, dibutylether, ethylene glycol dimethyl and diethyl ether, tetrahydrofuran and dioxane.

In general, from 80 to 300 kg, preferably from 100 to 200 kg, of solvent are employed per kg of ketimine.

The hydrolysis is preferably carried out using an inorganic acid, such as hydrochloric acid, sulfuric acid, phosphoric acid or nitric acid.

From 3 to 6 kg of a 2 to 4 normal aqueous solution of the acid are usually employed per kg of ketimine.

The reaction temperature is generally from 10 to 60° C., preferably from 20 to 40° C.

The hydrolysis is generally complete in from 0.5 to 3 hours.

An advantageous technical procedure in step b) is the following:

The ketimine is dissolved in the solvent with stirring, the mixture is brought to the desired reaction temperature, the aqueous acid is added and the mixture is stirred at this temperature for from 0.5 to 3 hours. The remaining acid is subsequently neutralized, for example using concentrated aqueous ammonia and the solvent is removed by distillation under reduced pressure.

The following procedure can then be used for further work-up of the reaction product:

The residue is suspended in an excess of dilute aqueous base (for example ammonia water) and filtered off, the filter material is, if desired, stirred repeatedly in a 30- to 50-fold amount of hot aqueous base (for example semiconcentrated aqueous ammonia) and again filtered off, and the filter material is washed with water until neutral and dried at 100° C. under reduced pressure. In order to remove benzophenone and further organic impurities, the dried crude product is subsequently extracted with petroleum ether.

Step c) of the process according to the invention, the reaction of the aminorylenedicarboximide of the general formula IV with a dicarbonate of the general formula V to give the rylene dye of the general formula I is carried out in the presence of a polar, aprotic solvent with base catalysis.

Particularly preferred dicarbonates of the general formula V are dialkyl carbonates, especially di($C_2$–$C_8$-alkyl) dicarbonates, such as diethyl dicarbonate, dipropyl dicarbonate, diisopropyl dicarbonate, di-n-butyl dicarbonate, di-sec-butyl dicarbonate, di-tert-butyl dicarbonate, di-tert-pentyl dicarbonate and bis(2-ethylhexyl) dicarbonate, dicycloalkyl dicarbonates, especially di($C_5$–$C_8$-cycloalkyl) dicarbonates, such as dicyclopentyl dicarbonate, dicyclohexyl dicarbonate and dicycloheptyl dicarbonate, dicycloalkylalkyl dicarbonates, such as bis(1- and 2-cyclohexylethyl) dicarbonate and bis(1,2- and 3-cyclohexylpropyl) dicarbonate, diaralkyl dicarbonates, especially diphenyl-$C_1$–$C_4$-alkyl dicarbonates, such as dibenzyl dicarbonate, bis(1- and 2-phenylethyl) dicarbonate and bis(1-, 2- and 3-phenylpropyl) dicarbonate, and diphenyldicycloalkyl-($C_1$–$C_4$-alkyl) dicarbonates, such as bis(1- and 2-cyclohexyl-2-phenyl) dicarbonate, bis(1-, 2- and 3-cyclohexyl-2-phenyl) dicarbonate and bis(1-, 2- and 3-cyclohexyl-3-phenyl) dicarbonate.

In general, from 2 to 5 mol, preferably from 3 to 4 mol of V are employed per mole of IV.

Particularly suitable polar, aprotic solvents are the ethers mentioned for step b), which are advantageously used in anhydrous (dried) form.

The amount of solvent is usually from 80 to 300 kg, preferably from 120 to 200 kg, per kg of IV.

Particularly suitable bases are nitrogen bases, especially tertiary aliphatic amines, preferably tri($C_1$–$C_4$-alkyl)amines, whose alkyl radicals may be identical or different and which are preferably used in combination with dialkylamino-substituted pyridines. Very particular preference is given to combinations of tri($C_2$–$C_4$-alkyl)amines, such as triethylamine, diisopropylethylamine and tributylamine, with 4-(N,N-dimethylamino)pyridine in a molar ratio of from 4:1 to 1:1, in particular of about 2:1.

In general, from 5 to 20 mol %, preferably about 10 mol % of base, based on V, are employed.

The reaction temperature is generally from 20 to 70° C., preferably from 35 to 50° C.

The reaction time is usually form 4 to 20 hours.

An advantageous technical procedure in step c) is the following:

The solvents, the aminorylene-3,4-dicarboximide of general formula IV and the base are initially introduced under a protective-gas atmosphere, the dicarbonate of the general formula V is added, and the mixture is stirred at the desired reaction temperature under a protective gas for from 4 to 20 hours. In order to work up the rylene dye of the general formula I, from about 70 to 80% by vol. of the solvent are subsequently removed by distillation under reduced pressure, a 2- to 4-fold amount of an aliphatic alcohol, for example methanol, is slowly added, and the precipitation of the rylene dye of the general formula I is completed by cooling to from 3 to 6° C., and the dye of the general formula I is filtered off and dried at 100° C. under reduced pressure.

The purity of the resultant rylene dyes of the general formula I is generally >97% and is generally adequate for use. For particular requirements, the purity can be increased by recrystallization from a halogenated hydrocarbon, such as methylenechloride or chloroform, or an aromatic solvent, such as benzene, toluene or xylene, or by column chromatography on silica gel using chloroform as eluent.

The process according to the invention enables the preparation of the rylene dyes of the general formula I and their intermediates in an advantageous economical manner. The purity of the products obtained in the individual process steps is generally >95% without further purification, and the yield over all process steps, in each case based on the rylene-3,4-dicarboximide derivative employed, is generally >60%.

The rylene dyes of the general formula I according to the invention are highly suitable for homogeneous coloring of high-molecular-weight organic and inorganic materials, in particular, for example, plastics, especially thermoplastics, surface coatings and printing inks, and oxidic layer systems.

A particularly advantageous property of the rylene dyes of the general formula I according to the invention is their thermochromicity, i.e. the irreversible conversion of the dyes from a molecular species having a primary color A into a structurally different species having a secondary color B. The thermochromic effect is induced by warming the colored material to temperatures above the conversion temperature of the rylene dye of the general formula I. The primary and/or secondary color of the colored material can in addition be varied in a simple manner by employing rylene dyes of the general formula I according to the invention in the form of a mixture with one another, with the thermochromic rylene dyes disclosed in WO-A-01/16109, unpublished at the priority date of the present invention, and/or with conventional pigments and dyes.

The thermochromicity of the rylene dyes of the general formula I according to the invention can in addition advantageously be utilized for the production of laser-markable or laser-inscribable colorings. Through a suitable choice of the substituent R', the conversion temperature of the rylene dyes of the general formula I can be set specifically for this application, which was unexpected. Thus, the conversion temperatures of rylene dyes of the formula I according to the invention in which R' is primary or secondary alkyl or aralkyl are generally >280° C. These rylene dyes of the general formula I can be incorporated into classical thermoplastics (for example polystyrene, poly(acrylonitrile-butadiene-styrene), poly(styrene-acrylonitrile), polycarbonate, polymethyl methacrylate or polyethylene terephthalate) in a conventional manner (for example by extrusion or injection molding) and used for industrial laser marking or inscription.

A laser-markable or laser-inscribable color can be produced using the rylene dyes of the general formula I according to the invention (or mixtures thereof with one another, with the thermochromic rylene dyes disclosed in WO-A-01/16109, unpublished at the priority date of te present invention, and/or with other colorants) in combination with one or more transparent or translucent, organic or inorganic (N)IR absorbers having, in particular, a neutral or only weak inherent color in the visible region which converts the incident (N)IR laser energy into the thermal energy needed for the thermochromic conversion.

For this purpose, conventional, commercially available (N)IR absorbers, for example those from the classes of the methines, azamethines, transition-metal dithiolenes, squaric acid derivatives, phthalocyanines, naphthalocyanines, amidinium and iminium salts and in particular quaterrylene tetracarboxylic acid derivatives can be used. For use together with semiconductor lasers, particular preference is given to absorbers having an absorption maximum at from 780 to 850 nm, and for use together with conventional Nd-YAG lasers, particular preference is given to absorbers having an absorption maximum at about 1064 nm, in each case having a gram absorptivity of at least 50 at the absorption maximum.

EXAMPLES

A) Preparation of Rylene Dyes of the Formula I According to the Invention a) Preparation of the Ketimines Examples 1 to 6

A solution, stirred under a protective gas, of k mmol of the transition-metal catalyst tris(benzylideneacetone) dipalladium(0) and c $\mu$mol of the cocatalyst 2,2"-bis (diphenylphosphino)-1,1'-binaphthyl (racemate) in $a_1$ l of anhydrous toluene was heated at 100° C. for 12 h after addition of $x_1$ g (18 mmol) of the monobromorylene-3,4-dicarboximide of the general formula II, 6.52 g (36 mmol) of benzophenonimine and 3.46 g of sodium tert-butoxide.

After the mixture had been cooled to room temperature, the insoluble constituents had been filtered off and the solvents had been removed by distillation under reduced pressure, the crude product was dissolved in as little chloroform or methylene chloride as possible with gentle warming. After filtration, the product was re-precipitated by careful addition of a five-fold amount of petroleum ether (boiling range 60–90° C.), filtered off and dried at 100° C. under reduced pressure.

Further details on these experiments and their results are shown in Table 1.

TABLE 1

| Ex. | $x_1$ [g] | Bromorylene-3,4-dicarboximide II | k [mmol] | c [μmol] | $a_1$ [l] | Yield [g]/[%] | Appearance | m.p. [° C.] |
|---|---|---|---|---|---|---|---|---|
| 1 | 12.5 | 11-Bromo-N-dodecylterrylene-3,4-dicarboximide | 0.35 | 5.5 | 1.8 | 11.4/80 | blue-green, microcrystalline | >300 |
| 2 | 11.4 | 11-Bromo-N-(p-methoxyphenyl)terrylene-3,4-dicarboximide | 0.35 | 5.5 | 1.8 | 11.6/88 | blue-green, microcrystalline | >300 |
| 3 | 12.3 | 11-Bromo-N-(2,6-diisopropylphenyl)-terrylene-3,4-dicarboximide | 0.35 | 5.5 | 1.8 | 12.0/85 | blue-green, crystalline | >300 |
| 4 | 14.7 | 13-Bromo-N-dodecylquaterrylene-3,4-dicarboximide | 0.50 | 8.0 | 2.0 | 13.0/79 | black-brown, crystalline | >300 |
| 5 | 13.6 | 13-Bromo-N-(p-methoxyphenyl)quaterrylene-3,4-dicarboximide | 0.50 | 8.0 | 2.0 | 13.2/86 | black-brown, crystalline | >300 |
| 6 | 14.6 | 13-Bromo-N-(2,6-diisopropylphenyl)-quaterrylene-3,4-dicarboximide | 0.50 | 10.0 | 2.0 | 12.9/79 | black-brown, crystalline | >300 |

Analytical Data for Example 1:

11-(Diphenylmethyleneimino)-N-dodecylterrylene-3,4-dicarboximide:

Elemental analysis (% by weight calc./found): C, 86.3/86.1; H, 6.1/6.2; N, 3.5/3.5; 0:4.0/4.1; Mass (FD, 8 kV): m/e=792.4 (M$^+$, 100%).

Analytical Data for Example 2:

11-(Diphenylmethyleneimino)-N-(p-methoxyphenyl)terrylene-3,4-dicarboximide:

Elemental analysis (% by weight calc./found): C, 85.5/85.4; H, 4.1/4.0; N, 3.8/3.9; O, 6.6/6.7. Mass (FD, 8 kV): m/e=730.4 (M$^+$, 100%).

Analytical Data for Example 3:

11-(Diphenylmethyleneimino)-N-(2,6-diisopropylphenyl)terrylene-3,4-dicarboximide:

Elemental analysis (% by weight calc./found): C, 87.2/87.0; H, 5.1/5.2; N, 3.6/3.6; O, 4.1/4.2. Mass (FD, 8 kV): m/e=784.3 (M$^+$, 100%).

Analytical Data for Example 4:

13-(Diphenylmethyleneimino)-N-dodecylquaterrylene-3,4-dicarboximide:

Elemental analysis (% by weight calc./found): C, 87.7/87.4; H, 5.7/5.8; N, 3.0/3.1; O, 3.5/3.7. Mass (FD, 8 kV): m/e=916.4 (M$^+$, 100%).

Analytical Data for Example 5:

13-(Diphenylmethyleneimino)-N-(p-methoxyphenyl)quaterrylene-3,4-dicarboximide:

Elemental analysis (% by weight calc./found): C, 87.1/87.3; H, 4.0/3.9; N, 3.3/3.3; O, 5.6/5.5. Mass (FD, 8 kV): m/e=854.2 (M$^+$, 100%).

Analytical Data for Example 6:

13-(Diphenylmethyleneimino)-N-(2,6-diisopropylphenyl)-quaterrylene-3,4-dicarboximide:

Elemental analysis (% by weight calc./found): C, 88.5/88.0; H, 4.9/5.0; N, 3.1/3.0; O, 3.5/3.9. Mass (FD, 8 kV): m/e=908.3 (M$^+$, 100%).

b) Preparation of aminorylene-3,4-dicarboximide IV

Examples 7 to 12

A solution of 10 g ($x_2$ mmol) of the ketimine from Examples 1 to 6 in $a_2$ l of 1,4-dioxane was stirred at $T_2$° C. for $t_2$ hours after addition of 50 ml of 2 molar aqueous hydrochloric acid.

After the reaction mixture has been neutralized using 25% strength by weight aqueous ammonia solution and the solvent has been removed by distillation under reduced pressure, the residue was suspended in a mixture of 1 l of water and 50 ml of concentrated aqueous ammonia solution in order to remove inorganic impurities, filtered off, again suspended twice, with interim filtration, in 1 l of hot 20% strength aqueous ammonia solution each time and then filtered. After hot extraction with petroleum ether (boiling range 60–90°$^9$ C.), the crude product was subsequently freed from benzophenone and other organic impurities and then dried at 100° C. under reduced pressure.

Further details on these experiments and their results are shown in Table 2.

TABLE 2

| Ex. | $x_2$ [mmol] | Ketimine from Ex. | $a_2$ [l] | $t_2$ [h] | $T_2$ [° C.] | Yield [g]/[%] | Appearance | m.p. [° C.] |
|---|---|---|---|---|---|---|---|---|
| 7 | 12.6 | 1 | 1.2 | 1.0 | 30 | 7.5/95 | blue-green, crystalline | >300 |
| 8 | 13.7 | 2 | 1.2 | 1.0 | 30 | 7.3/94 | blue-green, crystalline | >300 |
| 9 | 12.7 | 3 | 1.2 | 1.0 | 30 | 7.3/92 | blue-green, micro-crystalline | >300 |
| 10 | 10.9 | 4 | 1.8 | 1.5 | 40 | 7.5/91 | black-brown, crystalline | >300 |
| 11 | 11.7 | 5 | 1.8 | 1.5 | 40 | 7.6/94 | black-brown, crystalline | >300 |
| 12 | 11.0 | 6 | 1.8 | 1.5 | 40 | 7.6/93 | black-brown, crystalline | >300 |

Analytical Data for Example 7:

11-Amino-N-dodecylterrylene-3,4-dicarboximide:

Elemental analysis (% by weight calc./found): C, 84.0/84.2; H, 6.4/6.5; N, 4.5/4.3; O, 5.1/4.9. Mass (FD, 8 kV): m/e=628.4 (M$^+$, 100%).

Analytical Data for Example 8:

11-Amino-N-(p-methoxyphenyl)terrylene-3,4-dicarboximide:

Elemental analysis (% by weight calc./found): C, 82.7/82.3; H, 3.9/4.1; N, 4.9/5.1; O, 8.5/8.4. Mass (FD, 8 kv): m/e=566.2 (M$^+$, 100%).

Analytical Data for Example 9

11-Amino-N-(2,6-diisopropylphenyl)terrylene-3,4-dicarboximide:

Elemental analysis (% by weight calc./found): C, 87.2/87.0; H, 5.1/5.2; N, 3.6/3.6; O, 4.1/4.2. Mass (FD, 8 kV): m/e=620.3 (M$^+$, 100%).

Analytical Data for Example 10:

13-Amino-N-dodecylquaterrylene-3,4-dicarboximide:

Elemental analysis (% by weight calc./found): C, 86.1/86.4; H, 5.9/5.7; N, 3.7/3.7; O, 4.3/4.2. Mass (FD, 8 kV): m/e=752.6 (M$^+$, 100%).

Analytical Data for Example 11

13-Amino-N-(p-methoxyphenyl)quaterrylene-3,4-dicarboximide:

Elemental analysis (% by weight calc./found): C, 85.2/85.2; H, 3.8/3.9; N, 4.1/4.0; O, 7.0/6.9. Mass (FD, 8 kV): m/e=690.3 ($M^+$, 100%).

Analytical Data for Example 12

13-Amino-N-(2,6-diisopropylphenyl)quaterrylene-3,4-dicarboximide:

Elemental analysis (% by weight calc./found): C, 88.5/88.0; H, 4.9/5.0; N, 3.1/3.0; O, 3.5/3.9. Mass (FD, 8 kV): m/e=744.4 ($M^+$, 100%).

c) Preparation of Rylene Dyes of the Formula I

Examples 13 to 25

A solution, stirred under a protective gas, of 49 mg (0.4 mmol) of 4-(N,N-dimethylamino)pyridine, 408 mg (0.8 mmol) of triethylamine and $x_3$ g (2 mmol) of the aminorylene-3,4-dicarboximide from Examples 7 to 12 in 200 ml of anhydrous dioxane was heated at 45° C. for $t_3$ hours after addition of y g (8 mmol) of the dicarbonate of the formula V.

After 80% by vol. of the solvent had been removed by the distillation under reduced pressure, the precipitation of the product was completed by slow addition of 500 ml of methanol and cooling to from 3 to 6° C. The precipitated product was filtered off, washed with methanol and dried at 100° C. under reduced pressure.

The melting points of all rylene dyes of the formula I obtained were above the thermal conversion temperature (elimination of $CO_2$ and alkene or aralkene).

Further details on these experiments and their results are shown in Table 3.

Analytical Data for Example 13:

11-(Diethoxycarbonyl)amino-N-(dodecyl)terrylene-3,4-dicarboximide:

Elemental analysis (% by weight calc./found): C, 77.7/77.7; H, 6.3/6.5; N, 3.6/3.5; O, 12.4/12.2. Mass (MALDI-TOF): m/e=772.2 ($M^+$, 100%); IR (KBr): ν=1698 (s, C=O), 1665 (s, C=O), 1500 (s) $cm^{-1}$; UV/VIS (NMP): $\lambda_{max}$ (ε)=580 (44000), 646 (49900) nm.

Analytical Data for Example 14:

11-(Di-sec-butoxycarbonyl)amino-N-(4-methoxyphenyl)terrylene-3,4-dicarboximide:

Elemental analysis (% by weight calc./found): C, 76.8/76.7; H, 5.0/4.9; N, 3.7/3.7; O, 14.6/14.7. Mass (MALDI-TOF): m/e=766.6 ($M^+$, 100%); IR (KBr): ν=1701 (s, C=O), 1668 (s, C=O) $cm^{-1}$; UV/VIS (NMP): $\lambda_{max}$ (ε)=576 (44370), 639 (43530) nm.

Analytical Data for Example 15:

11-(Diethoxycarbonyl)amino-N-(2,6-diisopropylphenyl)terrylene-3,4-dicarboximide:

Elemental analysis (% by weight calc./found): C, 78.5/78.3; H, 5.3/5.3; N, 3.65/3.7; O, 12.55/12.7. Mass (MALDI-TOF): m/e=764.3 ($M^+$, 100%); IR (KBr): ν=1700 (s, c=O), 1666 (s, C=O), 1501 (s) $cm^{-1}$; UV/VIS (NMP): $\lambda_{max}$ (ε)=577 (45080), 644 (46110) nm.

Analytical Data for Example 16:

11-(Di-n-butoxycarbonyl)amino-N-(2,6-diisopropylphenyl)terrylene-3,4-dicarboximide:

Elemental analysis (% by weight calc./found): C, 79.0/79.3; H, 5.9/5.8; N, 3.4/3.5; O, 11.7/11.4. Mass (MALDI-TOF): m/e=820.1 ($M^+$, 100%); IR (KBr): ν=1702 (s, C=O), 1667 (s, C=O), 1499 (s) $cm^{-1}$; UV/VIS (NMP): $\lambda_{max}$ (ε)=577 (43980), 645 (44230) nm.

Analytical Data for Example 17:

11-(Di-tert-butoxycarbonyl)amino-N-(2,6-diisopropylphenyl)-terrylene-3,4-dicarboximide:

TABLE 3

| Ex. | $x_3$ [g] | Aminorylene-3,4-dicarboximide IV from Ex. | y [g] | Dicarbonate V | $t_3$ [h] | Yield [g]/[%] | Appearance |
| --- | --- | --- | --- | --- | --- | --- | --- |
| 13 | 1.26 | 7 | 1.30 | Diethyl dicarbonate | 10 | 1.19/77 | deep blue, microcrystalline |
| 14 | 1.13 | 8 | 1.75 | Di-sec-butyl dicarbonate | 10 | 1.23/80 | deep blue, microcrystalline |
| 15 | 1.24 | 9 | 1.30 | Diethyl dicarbonate | 10 | 1.19/78 | deep blue, microcrystalline |
| 16 | 1.24 | 9 | 1.75 | Di-n-butyl dicarbonate | 10 | 1.23/75 | deep blue, microcrystalline |
| 17 | 1.24 | 9 | 1.75 | Di-tert-butyl dicarbonate | 10 | 1.38/84 | deep blue, microcrystalline |
| 18 | 1.24 | 9 | 2.29 | Dibenzyl dicarbonate | 10 | 1.40/79 | deep blue, microcrystalline |
| 19 | 1.51 | 10 | 1.75 | Di-tert-butyl dicarbonate | 10 | 1.62/85 | blue-green, microcrystalline |
| 20 | 1.38 | 11 | 1.30 | Diethyl dicarbonate | 6 | 1.42/85 | blue-green, microcrystalline |
| 21 | 1.49 | 12 | 1.30 | Diethyl dicarbonate | 6 | 1.49/84 | blue-green, microcrystalline |
| 22 | 1.49 | 12 | 1.75 | Di-n-butyl dicarbonate | 6 | 1.51/80 | blue-green, microcrystalline |
| 23 | 1.49 | 12 | 1.75 | Di-sec-butyl dicarbonate | 6 | 1.55/82 | blue-green, microcrystalline |
| 24 | 1.49 | 12 | 1.75 | Di-tert-butyl dicarbonate | 6 | 1.59/84 | blue-green, microcrystalline |
| 25 | 1.49 | 12 | 2.29 | Dibenzyl dicarbonate | 6 | 1.60/79 | blue-green, microcrystalline |

Elemental analysis (% by weight calc./found): C, 79.0/ 78.8; H, 5.9/6.0; N, 3.4/3.5; O, 11.7/11.7. Mass (MALDI-TOF): m/e=820.5 (M$^+$, 100%); IR (KBr): ν=1749 (s, C═O), 1702 (s, C═O), 1664 (s, C═O), 1594 (s, C═O) cm$^{-1}$; UV/VIS (NMP): $\lambda_{max}$ (ε)=579 (44270), 643 (44120) nm.

Analytical Data for Example 18:

11-(Dibenzyloxycarbonyl)amino-N-(2,6-diisopropylphenyl)-terrylene-3,4-dicarboximide:

Elemental analysis (% by weight calc./found): C, 81.1/ 80.7; H, 5.0/5.1; N, 3.2/3.2; O, 10.8/11.0. Mass (MALDI-TOF): m/e=888.6 (M$^+$, 100%); IR (KBr): ν=1700 (s, C═O), 1665 (s, C═O), 1498 (s) cm$^{-1}$; UV/VIS (NMP): $\lambda_{max}$ (ε)=577 (43980), 645 (46800) nm.

Analytical Data for Example 19:

13-(Di-tert-butoxycarbonyl)amino-N-(dodecyl) quaterrylene-3,4-dicarboximide:

Elemental analysis (% by weight calc./found): C, 80.7/ 81.0; H, 6.3/6.1; N, 2.9/2.8; O, 10.1/10.1. Mass (MALDI-TOF): m/e=952.2 (M$^+$, 100%); IR (KBr): ν=1748 (s, C═O), 1699 (s, C═O), 1665 (s, C═O), 1593 (s, C═O) cm$^{-1}$; UV/VIS (NMP): $\lambda_{max}$ (ε)=680 (75000), 744 (78760) nm.

Analytical Data for Example 20:

13-(Diethoxycarbonyl)amino-N-(4-methoxyphenyl) quaterrylene-3,4-dicarboximide:

Elemental analysis (% by weight calc./found): C, 79.1/ 78.7; H, 4.1/4.3; N, 3.4/3.5; O, 13.4/13.4. Mass (MALDI-TOF): m/e=834.4 (M$^+$, 100%); IR (KBr): ν=1700 (s, C═O), 1667 (s, C═O), 1504 (s) cm$^{-1}$; UV/VIS (NMP): $\lambda_{max}$ (ε)=677 (75580), 738 (73920) nm.

Analytical Data for Example 21:

13-(Diethoxycarbonyl)amino-N-(2,6-diisopropylphenyl) quaterrylene-3,4-dicarboximide:

Elemental analysis (% by weight calc./found): C, 81.05/ 81.2; H, 5.0/5.0; N, 3.15/3.1; O, 10.8/10.7. Mass (FD, 8 kV): m/e=888.4 (M$^+$, 100%); IR (KBr): ν=1701 (s, C═O), 1667 (s, C═O), 1502 (s) cm$^{-1}$; UV/VIS (NMP): $\lambda_{max}$ (ε)=678 (74080), 742 (77640) nm.

Analytical Data for Example 22:

13-(Di-n-butoxycarbonyl)amino-N-(2,6-diisopropylphenyl)-quaterrylene-3,4-dicarboximide:

Elemental analysis (% by weight calc./found): C, 81.3/ 81.0; H, 5.5/6.0; N, 3.0/3.0; O, 10.2/10.0. Mass (FD, 8 kV): m/e=944.3 (M$^+$, 100%); IR (KBr): ν=1701 (s, C═O), 1668 (s, C═O), 1504 (s) cm$^{-1}$; UV/VIS (NMP): $\lambda_{max}$ (ε)=678 (72840), 741 (75210) nm.

Analytical Data for Example 23:

13-(Di-sec-butoxycarbonyl)amino-N-(2,6-diisopropylphenyl)-quaterrylene-3,4-dicarboximide:

Elemental analysis (% by weight calc./found): C, 81.3/ 81.1; H, 5.6/5.4; N, 3.0/3.1; O, 10.1/10.3. Mass (FD, 8 kV): m/e=944.2 (M$^+$, 100%); IR (KBr): ν=1702 (s, C═O), 1666 (s, C═O) cm$^{-1}$; UV/VIS (NMP): $\lambda_{max}$ (ε)=679 (73050), 740 (74990) nm.

Analytical Data for Example 24:

13-(Di-tert-butoxycarbonyl)amino-N-(2,6-diisopropylphenyl)-quaterrylene-3,4-dicarboximide:

Elemental analysis (% by weight calc./found): C, 81.3/ 81.0; H, 5.6/5.9; N, 3.0/3.0; O, 10.1/10.1. Mass (FD, 8 kV): m/e=944.4 (M$^+$, 100%); IR (KBr): ν=1750 (s, C═O), 1700 (s, C═O), 1665 (s, C═O), 1593 (s, C═O) cm$^{-1}$; UV/VIS (NMP): $\lambda_{max}$ (ε)=680 (73820), 745 (73670) nm.

Analytical Data for Example 25:

13-(Dibenzyloxycarbonyl)amino-N-(2,6-diisopropylphenyl)-quaterrylene-3,4-dicarboximide:

Elemental analysis (% by weight calc./found): C, 83.0/ 83.3; H, 4.8/5.0; N, 2.8/2.7; O, 9.5/9.0. Mass (FD, 8 kV): m/e=1012.7 (M$^+$, 100%); IR (KBr): ν=1699 (s, C═O), 1666 (s, C═O), 1501 (s) cm$^{-1}$; UV/VIS (NMP): $\lambda_{max}$ (ε)=678 (73550), 742 (75800) nm.

B) Use of Rylene Dyes of the Formula I According to the Invention a) Preparation of High-Molecular-Weight Materials with a Thermochromic Coloring.

For the preparation of thermoplastics with a thermochromic coloring, in each case x g of the dye of the formula I and, if desired, z g of the transparent pigment P or of one of the thermochromic dyes F from WO-A-01/16109, unpublished at the priority date of the present invention, were mixed with 100 g of one of the matrix polymers PS: Polystyrene 144C crystal clear (BASF)
PMMA: Polymethyl methacrylate molding composition 7N crystal clear (Röhm) or
PC: Polycarbonate Makrolone® 2858 (Bayer)
and converted into a semi-finished product in a conventional manner by extrusion and injection molding.

In order to produce thermochromic surface coatings, a mixture of in each case x g of the dye of the formula I and 100 g of a solvent-based alkyd-melamine baking enamel (45% by weight of solids content) was shaken with 150 g of glass beads (diameter 3 mm) for 30 minutes in a Skandex instrument, then applied to metal sheeting using a knife coater and baked for 30 minutes at 130° C. (film thickness in the dried state 55±5 μm).

The thermochromic color change (primary color→secondary color) of the colored polymeric systems was induced by heating for 15 minutes at the respective conversion temperature T° C.

Further details on these experiments and their results are shown in Table 4.

TABLE 4

| Ex. | x [g] | Rylene dye I from Ex. | z [g] | Pigment P or thermochromic dye F | Polymeric system | Primary color | Secondary color | T [° C.] |
|---|---|---|---|---|---|---|---|---|
| 26 | 0.2 | 14 | — | — | PS | deep blue | green | 300 |
| 27 | 0.2 | 15 | — | — | PS | deep blue | green | 340 |
| 28 | 0.2 | 15 | — | — | PMMA | deep blue | green | 360 |
| 29 | 0.2 | 15 | — | — | PC | deep blue | green | 360 |
| 30 | 0.2 | 17 | — | — | PS | deep blue | green | 220 |
| 31 | 5.0 | 17 | — | — | varnish | deep blue | green | 190 |
| 32 | 0.2 | 21 | — | — | PS | blue-green | pale gray | 340 |
| 33 | 0.2 | 21 | — | — | PMMA | blue-green | pale gray | 360 |
| 34 | 0.2 | 21 | — | — | PC | blue-green | pale gray | 370 |
| 35 | 0.2 | 22 | — | — | PS | blue-green | pale gray | 310 |

TABLE 4-continued

| Ex. | x [g] | Rylene dye I from Ex. | z [g] | Pigment P or thermochromic dye F | Polymeric system | Primary color | Secondary color | T [° C.] |
|---|---|---|---|---|---|---|---|---|
| 36 | 0.2 | 23 | — | — | PS | blue-green | pale gray | 330 |
| 37 | 0.2 | 24 | — | — | PS | blue-green | pale gray | 220 |
| 38 | 5.0 | 24 | — | — | varnish | blue-green | pale gray | 190 |
| 39 | 0.1 | 15 | 0.225 | 4-(Diethoxycarbonyl)amino-N-(2,6-diisopropylphenyl)-naphthalene-1,8-dicarboximide | PS | deep blue | yellow-green | 340 |
| 40 | 0.1 | 21 | 0.225 | 4-(Diethoxycarbonyl)amino-N-(2,6-diisopropylphenyl)-naphthalene-1,8-dicarboximide | PS | blue-green | yellow-orange | 340 |
| 41 | 0.1 | 15 | 0.150 | 9-(Diethoxycarbonyl)amino-N-(2,6-diisopropylphenyl)perylene-3,4-dicarboximide | PS | deep blue | violet | 340 |
| 42 | 0.1 | 21 | 0.150 | 9-(Diethoxycarbonyl)amino-N-(2,6-diisopropylphenyl)perylene-3,4-dicarboximide | PS | brown | violet | 340 |
| 43 | 0.2 | 15 | 0.200 | C.I. Pigment Red 149 (Paliogen ® Rot K 3580) | PS | violet | gray-brown | 340 |
| 44 | 0.2 | 21 | 0.200 | C.I. Pigment Red 149 (Paliogen ® Rot K 3580) | PS | brown | red | 340 |
| 45 | 0.1 | 15 | 0.200 | C.I. Pigment Yellow 138 (Paliotol ® Gelb K 0961) | PS | green | yellow-brown | 340 |
| 46 | 0.1 | 21 | 0.200 | C.I. Pigment Yellow 138 (Paliotol ® Gelb K 0961) | PS | blue-green | yellow | 340 | b) Production of Laser-Markable or Laser-Inscribable Colorings

In order to produce laser-markable or laser-inscribable colorings, the dyes or dye mixtures from Examples 28, 33, 39 or 41 were incorporated into PMMA (Examples 28 and 33) or PS (Examples 39 and 41) as described under a), but with addition of y g of the (near) infrared absorber A.

The colored semi-finished product was subsequently marked using an Nd-YAG laser (emission wavelength of 1064 nm, nominal laser power 40 watts; scanning rate 1000 mm/s; Examples 47 and 50) or with a semiconductor laser diode (emission wavelength of 780 nm, nominal laser power 1 watt, scanning rate 100 mm/s; Examples 51 to 54).

Further details on these experiments and their results are shown in Table 5.

TABLE 5

| Ex. | Dyes I or mixtures from Ex. | y [g] | (N)IR absorber A | Color of the mark | Background color |
|---|---|---|---|---|---|
| 47 | 28 | 0.010 | (N)IR-Senzitizing Dye IR 1060-1 (methine dye; Esprit Inc.) | green | deep blue |
| 48 | 33 | 0.010 | (N)IR-Senzitizing Dye IR 1060-1 (methine dye; Esprit Inc.) | pale gray | blue-green |
| 49 | 39 | 0.010 | (N)IR-Senzitizing Dye IR 1060-1 (methine dye; Esprit Inc.) | yellow-green | deep blue |
| 50 | 41 | 0.010 | (N)IR-Senzitizing Dye IR 1060-1 (methine dye; Esprit Inc.) | violet | deep blue |
| 51 | 28 | 0.005 | (N)IR-Senzitizing Dye IR 800-1 (cyanine dye; Esprit Inc.) | yellow-green | deep blue |
| 52 | 39 | 0.005 | (N)IR-Senzitizing Dye IR 800-1 (cyanine dye; Esprit Inc.) | yellow-green | blue-green |
| 53 | 33 | 0.010 | N,N'-Bis(2,6-diisopropylphenyl)-quaterrylene-3,4:13,14-tetracarboxylic diimide | pale turquoise | blue-green |
| 54 | 41 | 0.010 | N,N'-Bis(2,6-diisopropylphenyl)-quaterrylene-3,4:13,14-tetracarboxylic diimide | violet | deep blue |

We claim:
1. A rylene dye of formula I

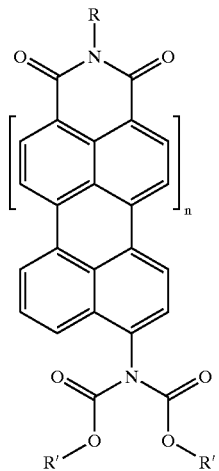

where
R is hydrogen;
  $C_1$–$C_{30}$-alkyl, whose carbon chain may be interrupted by one or more —O—, —S—, —NR$^1$—, —CO— and/or —SO$_2$— groups and which may be monosubstituted or polysubstituted by cyano, $C_1$–$C_6$-alkoxy, aryl, which may be substituted by $C_1$–$C_{18}$-alkyl or $C_1$–$C_6$-alkoxy, and/or a 5- to 7-membered heterocyclic radical which is bonded via a nitrogen atom and may contain further heteroatoms and may be aromatic;
aryl or hetaryl, each of which may be monosubstituted or polysubstituted by $C_1$–$C_{18}$-alkyl, $C_1$–$C_6$-alkoxy, cyano, —CONHR$^2$, —NHCOR$^2$ and/or aryl- or hetarylazo, each of which may be substituted by $C_1$–$C_{10}$-alkyl, $C_1$–$C_6$-alkoxy and/or cyano;
R' is $C_2$–$C_{30}$-alkyl, whose carbon chain may be interrupted by one or more —O— and/or —CO— groups and which may be monosubstituted or polysubstituted by cyano, $C_1$–$C_6$-alkoxy, $C_5$–$C_8$-cycloalkyl, whose carbon skeleton may be interrupted by one or more —O—, —S— and/or —NR$^1$— groups and which may be $C_1$–$C_6$-alkyl-substituted, aryl, which may be substituted by $C_1$–$C_{18}$-alkyl or $C_1$–$C_6$-alkoxy, and/or a 5- to 7-membered heterocyclic radical which is bonded via a nitrogen atom and which may contain further heteroatoms and which may be aromatic;
methyl, which is monosubstituted or disubstituted by aryl, hetaryl and/or $C_5$–$C_8$-cycloalkyl, each of which may be substituted by $C_1$–$C_{18}$-alkyl or $C_1$–$C_6$-alkoxy;
$C_5$–$C_8$-cycloalkyl, whose carbon skeleton may be interrupted by one or more —O—, —S— and/or —NR$^1$— groups and which may be monosubstituted or polysubstituted by $C_1$–$C_6$-alkyl;
R$^1$ is hydrogen or $C_1$–$C_6$-alkyl;
R$^2$ is hydrogen; $C_1$–$C_{18}$-alkyl; aryl or hetaryl, each of which may be substituted by $C_1$–$C_6$-alkyl, $C_1$–$C_6$-alkoxy and/or cyano;
n is 2 or 3.
2. A rylene dye of formula I as claimed in claim 1 where
R is hydrogen;
  $C_1$–$C_{30}$-alkyl, whose carbon chain may be interrupted by one or more —O— and/or —CO— groups which may be monosubstituted or polysubstituted by cyano, $C_1$–$C_6$-alkoxy, aryl, which may be substituted by $C_1$–$C_{18}$-alkyl or $C_1$–$C_6$-alkoxy, and/or a 5- to 7-membered heterocyclic radical which is bonded via a nitrogen atom and may contain further heteroatoms and may be aromatic;
aryl or hetaryl, each of which may be monosubstituted or polysubstituted by $C_1$–$C_{18}$-alkyl, $C_1$–$C_6$-alkoxy, cyano, —CONHR$^2$ or —NHCOR$^2$;
R' is $C_2$–$C_{30}$-alkyl, whose carbon chain may be interrupted by one or more —O— and/or —CO— groups and which may be monosubstituted or polysubstituted by $C_1$–$C_6$-alkoxy, $C_5$–$C_8$-cycloalkyl, whose carbon skeleton may be interrupted by one or more —O— and/or —NR$^1$— groups and which may be $C_1$–$C_6$-alkyl-substituted, and/or aryl, which may be substituted by $C_1$–$C_{18}$-alkyl or $C_1$–$C_6$-alkoxy; methyl, which is monosubstituted or disubstituted by aryl and/or $C_5$–$C_8$-cycloalkyl, each of which may be substituted by $C_1$–$C_{18}$-alkyl or $C_1$–$C_6$-alkoxy; p1 $C_5$–$C_8$-cycloalkyl, whose carbon skeleton may be interrupted by one or more —O— and/or —NR$^1$— groups and which may be monosubstituted or polysubstituted by $C_1$–$C_6$-alkyl.
3. A rylene dye of formula I as claimed in claim 1 where
R is hydrogen;
  $C_1$–$C_{30}$-alkyl, whose carbon chain may be interrupted by one or more —O— and/or —CO— groups which may be monosubstituted or disubstituted by $C_1$–$C_6$-alkoxy and/or aryl, which may be substituted by $C_1$–$C_{18}$-alkyl or $C_1$–$C_6$-alkoxy;
aryl, which may be monosubstituted or polysubstituted by $C_1$–$C_{18}$-alkyl, $C_1$–$C_6$-alkoxy and/or cyano;
R' is $C_2$–$C_{30}$-alkyl, whose carbon chain may be interrupted by one or more —O— groups and which may be monosubstituted or polysubstituted by $C_1$–$C_6$-alkoxy, $C_5$–$C_8$-cycloalkyl which may be $C_1$–$C_6$-alkyl-substituted, and/or aryl, which may be substituted by $C_1$–$C_{18}$-alkyl or $C_1$–$C_6$-alkoxy;
methyl, which is monosubstituted or disubstituted by aryl and/or $C_5$–$C_8$-cycloalkyl, each of which may be substituted by $C_1$–$C_{18}$-alkyl or $C_1$–$C_6$-alkoxy;
$C_5$–$C_8$-cycloalkyl, which may be monosubstituted or polysubstituted by $C_1$–$C_6$-alkyl.
4. A process for the preparation of a rylene dye of formula I as claimed in claim 1, which comprises:
a) reacting a bromorylene-3,4-dicarboximide of general formula II

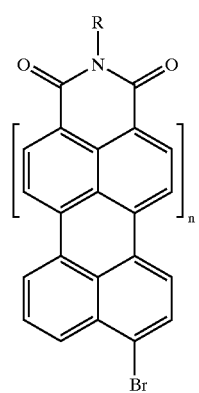

with a benzophenonimine of general formula III

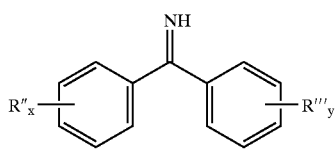

where
R", R'", independently of one another, are hydrogen, $C_1$–$C_6$-alkyl or $C_1$–$C_6$-alkoxy and x, y, independently of one another, are an integer from 1 to 3, in the presence of an aprotic organic solvent, a transition-metal catalyst system and a base in an aryl-N coupling reaction, b) hydrolyzing the resultant ketimine in the presence of an acid and in the presence of a polar, aprotic solvent to give an aminorylene-3,4-dicarboximide of general formula IV

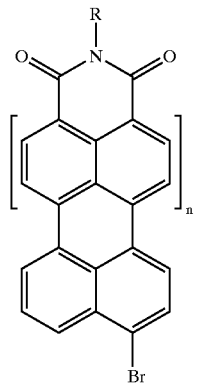

and c) subsequently reacting the compound of formula IV with a dicarbonate of general formula V

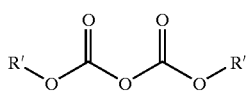

in the presence of a polar, aprotic solvent and in the presence of a base to give a rylene dye of formula I.

5. A process for the preparation of an aminorylene-3,4-dicarboximide of formula IV

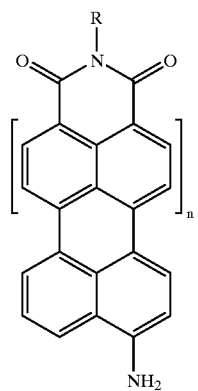

where

R is hydrogen;

$C_1$–$C_{30}$-alkyl, whose carbon chain may be interrupted by one or more —O—, —S—, —$NR^1$—, —CO— and/or —$SO_2$— groups and which may be monosubstituted or polysubstituted by cyano, $C_1$–$C_6$-alkoxy, aryl, which may be substituted by $C_1$–$C_{18}$-alkyl or $C_1$–$C_6$-alkoxy, and/or a 5- to 7-membered heterocyclic radical which is bonded via a nitrogen atom and may contain further heteroatoms and may be aromatic;

aryl or hetaryl, each of which may be monosubstituted or polysubstituted by $C_1$–$C_{18}$-alkyl, $C_1$–$C_6$-alkoxy, cyano, —$CONHR^2$, —$NHCOR^2$ and/or aryl- or hetarylazo, each of which may be substituted by $C_1$–$C_{10}$-alkyl, $C_1$–$C_6$-alkoxy and/or cyano;

$R^1$ is hydrogen or $C_1$–$C_6$-alkyl;

$R^2$ is hydrogen; $C_1$–$C_6$-alkyl; aryl hetaryl, each of which be substituted by $C_1$–$C_6$-alkyl, $C_1$–$C_6$-alkoxy and/or cyano;

n is 2 or 3, which comprises a) reacting a bromorylene-3,4-dicarboximide of formula II

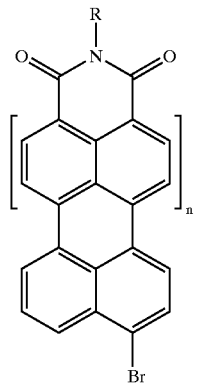

with a benzophenonimine of formula III

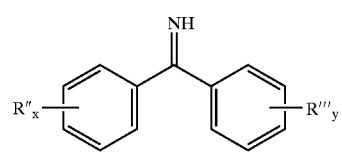

where

R", R'", independently of one another, are hydrogen, $C_1$–$C_6$-alkyl or $C_1$–$C_6$-alkoxy and x, y, independently of one another, are an integer from 1 to 3, in the presence of an aprotic organic solvent, a transition-metal catalyst system and a base in an aryl-N coupling reaction, and b) hydrolyzing the resultant ketimine in the presence of an acid and in the presence of a polar, aprotic solvent.

6. An aminorylene-3,4-dicarboximide of formula IV

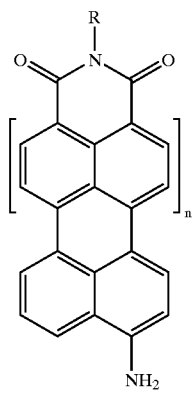

IV where

R is hydrogen;
C$_1$–C$_{30}$-alkyl, whose carbon chain may be interrupted by one or more —O—, —S—, —NR$^1$—, —CO— and/or —SO$_2$— groups and which may be mono-substituted or polysubstituted by cyano, C$_1$–C$_6$-alkoxy, aryl, which may be substituted by C$_1$–C$_{18}$-alkyl or C$_1$–C$_6$-alkoxy, and/or a 5- to 7-membered heterocyclic radical which is bonded via a nitrogen atom and may contain further heteroatoms and may be aromatic;
aryl or hetaryl, each of which may be monosubstituted or polysubstituted by C$_1$–C$_{18}$-alkyl, C$_1$–C$_6$-alkoxy, cyano, —CONHR$^2$, —NHCOR$^2$ and/or aryl- or hetarylazo, each of which may be substituted by C$_1$–C$_{10}$-alkyl, C$_1$–C$_6$-alkoxy and/or cyano;
R' is hydrogen or C$_1$–C$_6$-alkyl;
R$^2$ is hydrogen, C$_1$–C$_{18}$-alkyl; aryl or hetaryl, each of which may be substituted by C$_1$–C$_6$-alkyl, C$_1$–C$_6$-alkoxy and/or cyano;
n is 2 or 3.

7. A composition, comprising:
the rylene dye of formula I as claimed in claim 1, and a high-molecular weight organic material or a high-molecular weight inorganic material.

8. A composition, comprising:
the rylene dye of formula I as claimed in claim 2, and a high-molecular weight organic material or a high-molecular weight inorganic material.

9. A composition, comprising:
the rylene dye of formula I as claimed in claim 3, and a high-molecular weight organic material or a high-molecular weight inorganic material.

10. A plastic, a surface coating, a printing ink, or an oxidic layer system, comprising:
the composition as claimed in claim 7.

11. A plastic, a surface coating, a printing ink, or an oxidic layer system, comprising:
the composition as claimed in claim 8.

12. A plastic, a surface coating, a printing ink, or an oxidic layer system, comprising:
the composition as claimed in claim 9.

13. A method of coloring high-molecular-weight organic or inorganic materials comprising:
mixing high-molecular-weight organic or inorganic materials with the rylene dye of formula I as claimed in claim 1.

14. A method of making laser markings or inscriptions comprising:
irradiating the surface coating, printing ink, or oxidic layer according to claim 10, with a laser.

* * * * *